(12) United States Patent
Rucinski

(10) Patent No.: US 9,629,953 B2
(45) Date of Patent: Apr. 25, 2017

(54) DEVICE AND METHOD FOR ABSCESS IRRIGATION

(75) Inventor: Paul J. Rucinski, Gainesville, FL (US)

(73) Assignee: INNOVATION TECHNOLOGIES, INC., Gainesville, FL (US)

( * ) Notice: Subject to any disclaimer, the term of this patent is extended or adjusted under 35 U.S.C. 154(b) by 1056 days.

(21) Appl. No.: 13/206,043

(22) Filed: Aug. 9, 2011

(65) Prior Publication Data

US 2012/0035559 A1    Feb. 9, 2012

Related U.S. Application Data

(60) Provisional application No. 61/371,981, filed on Aug. 9, 2010.

(51) Int. Cl.
*A61M 3/02*     (2006.01)
*A61M 31/00*    (2006.01)

(52) U.S. Cl.
CPC ........ *A61M 3/0233* (2013.01); *A61M 3/0279* (2013.01); *A61M 3/0262* (2013.01)

(58) Field of Classification Search
CPC .................................................. A61M 3/0262
USPC ..................................... 604/278, 279, 94.01
See application file for complete search history.

(56) References Cited

U.S. PATENT DOCUMENTS

| | | | | |
|---|---|---|---|---|
| 85,995 A * | 1/1869 | Buffon | .......................... | 604/278 |
| 212,177 A * | 2/1879 | Berger | .......................... | 604/278 |
| 214,552 A * | 4/1879 | Connable | ..................... | 604/215 |
| 497,757 A * | 5/1893 | Ackley | ........................... | 604/37 |
| 631,899 A * | 8/1899 | Mellon | ......................... | 604/278 |
| 770,739 A * | 9/1904 | Coleman | ...................... | 604/278 |
| 987,910 A * | 3/1911 | Piper | ............................. | 604/250 |
| 1,534,852 A * | 4/1925 | Hunter | ............................ | 604/84 |
| 1,638,532 A * | 8/1927 | Kallmeyer | ................... | 604/279 |
| 1,841,406 A * | 1/1932 | Galazin | .......................... | 604/30 |
| 2,087,511 A * | 7/1937 | Gould | ........................... | 604/279 |
| 2,199,844 A * | 5/1940 | Tucker | ............................ | 604/84 |
| 2,616,421 A * | 11/1952 | Greenberg | ................... | 604/278 |
| 2,664,088 A * | 12/1953 | Hoch | ............................ | 604/275 |
| 2,739,592 A * | 3/1956 | Western et al. | ............... | 604/215 |
| 2,764,975 A * | 10/1956 | Greenberg | ...................... | 600/35 |
| 3,109,427 A * | 11/1963 | Davidson | ..................... | 604/212 |

(Continued)

FOREIGN PATENT DOCUMENTS

WO    WO 96/04037 A1    2/1996
WO    WO 00/15279       3/2000

(Continued)

OTHER PUBLICATIONS

Definition of "contiguous", The American Heritage(R) Dictionary of the English Language, 2000.*

*Primary Examiner* — Paula L Craig
(74) *Attorney, Agent, or Firm* — Saliwanchik, Lloyd & Eisenschenk

(57) ABSTRACT

The subject invention provides novel, inexpensive, and highly effective methods and devices for convenient and effective irrigation of abscesses, puncture wounds, and similar types of deep tissue wounds. In one embodiment the subject invention provides a discharge apparatus for a reservoir housing containing irrigation solution, wherein the discharge apparatus has a specifically designed nozzle for insertion into a wound opening and through which a sufficient volume of the irrigation solution can pass at an appropriate pressure.

8 Claims, 12 Drawing Sheets

(56) References Cited

U.S. PATENT DOCUMENTS

| | | | |
|---|---|---|---|
| 3,225,763 A * | 12/1965 | Waterman | 604/192 |
| 3,439,675 A * | 4/1969 | Cohen | 604/192 |
| 3,469,575 A * | 9/1969 | Vass et al. | 604/278 |
| 3,577,982 A * | 5/1971 | La Par | 600/435 |
| 3,589,362 A * | 6/1971 | Zamarra | 604/212 |
| 3,648,696 A * | 3/1972 | Keith | 604/310 |
| 3,771,523 A * | 11/1973 | Zanca | 604/212 |
| 3,802,435 A * | 4/1974 | Claasen | 604/200 |
| 3,916,896 A * | 11/1975 | Ballard | 604/103.11 |
| 4,206,756 A * | 6/1980 | Grossan | 604/39 |
| 4,309,995 A * | 1/1982 | Sacco | 604/259 |
| 4,692,140 A * | 9/1987 | Olson | 604/40 |
| 4,898,588 A * | 2/1990 | Roberts | 604/187 |
| 4,923,448 A * | 5/1990 | Ennis, III | 604/239 |
| 5,133,701 A * | 7/1992 | Han | 604/289 |
| 5,201,893 A * | 4/1993 | Holloway et al. | 206/571 |
| 5,217,439 A * | 6/1993 | McClusky | 604/275 |
| 5,224,940 A * | 7/1993 | Dann et al. | 604/290 |
| 5,309,899 A * | 5/1994 | Ginsberg | 604/38 |
| 5,376,003 A * | 12/1994 | Rizkalla | 433/116 |
| 5,464,390 A * | 11/1995 | Arnett et al. | 604/35 |
| 5,496,290 A * | 3/1996 | Ackerman | 604/268 |
| 5,527,275 A | 6/1996 | Ginsberg | |
| 5,735,833 A * | 4/1998 | Olson | 604/289 |
| 5,830,197 A | 11/1998 | Rucinski | |
| 5,843,043 A * | 12/1998 | Markus | 604/239 |
| 6,156,004 A * | 12/2000 | Tremaine et al. | 604/27 |
| 6,210,358 B1 * | 4/2001 | Roger | 604/43 |
| 6,210,381 B1 * | 4/2001 | Morse | 604/289 |
| 6,234,110 B1 * | 5/2001 | Xavier | 119/14.47 |
| 6,293,929 B1 * | 9/2001 | Smith et al. | 604/289 |
| 6,379,341 B1 | 4/2002 | Cho | |
| 6,394,996 B1 * | 5/2002 | Lawrence et al. | 604/540 |
| 6,468,253 B1 | 10/2002 | Rucinski | |
| 6,755,196 B2 * | 6/2004 | Musso et al. | 128/849 |
| 7,186,243 B1 * | 3/2007 | Mezzoli | 604/279 |
| D556,595 S | 12/2007 | Rucinski | |
| D588,692 S | 3/2009 | Rucinski | |
| 7,540,860 B2 * | 6/2009 | Stamler | 604/268 |
| D638,120 S * | 5/2011 | Schultz | D24/127 |
| D639,425 S * | 6/2011 | Schultz | D24/127 |
| 2003/0229322 A1 * | 12/2003 | MacRae | 604/275 |
| 2005/0124946 A1 * | 6/2005 | Landau et al. | 604/317 |
| 2005/0148958 A1 * | 7/2005 | Rucinski | 604/290 |
| 2005/0159713 A1 * | 7/2005 | McPherson | 604/279 |
| 2006/0122563 A1 * | 6/2006 | Ziv | 604/187 |
| 2009/0202665 A1 * | 8/2009 | Javer et al. | 424/744 |

FOREIGN PATENT DOCUMENTS

| | | |
|---|---|---|
| WO | WO 02/07799 | 1/2002 |
| WO | WO 02/38203 A1 | 5/2002 |

* cited by examiner

DEVICE AND METHOD FOR ABSCESS IRRIGATION

CROSS-REFERENCE TO A RELATED APPLICATION

This application claims the benefit of U.S. provisional application Ser. No. 61/371,981, filed Aug. 9, 2010, which is incorporated herein by reference in its entirety.

BACKGROUND OF THE INVENTION

An abscess is a localized collection of pus within the body. Abscesses are typically caused when the body tries to fight an infection within the tissues of the body, sending white blood cells to fight further infection. The blood cells collect around the initial site of infection, accumulating to form pus. As the white blood cells die and the infection increases, the surrounding healthy tissues form an "abscess wall", or capsule, around the pus in an attempt to prevent it from infecting neighboring structures. However, this encapsulation of the pus and the abscess wall tend to prevent further immune cells from attacking bacteria in the pus, or from reaching the causative organism or foreign object.

Abscesses can develop in many parts of the body, but they often involve the skin surface. Skin abscesses are often referred to as boils. Unlike other infections, antibiotics alone may not cure a large abscess. Usually, large abscesses must open and drain to improve. Although sometimes an abscess will open and drain spontaneously, it often needs to be opened and drained (incision and drainage) by a health care provider.

The standard treatment procedure is for a doctor to use a local anesthetic to numb the affected area. A sedative may even be needed if the abscess is large. Using a scalpel, the abscess is lanced and allowed to drain, removing the pus and any other debris from the area. To minimize scarring, it can be preferable to make the incision only as large as necessary to promote drainage. Antibiotics and hot compresses are usually prescribed. Large abscesses can result in an abscess pocket remaining under the skin after all the pus is drained, which usually necessitates repeated fluid irrigation during the healing process to wash away accumulated debris, sloughed tissue, or recurring pus formation. Ideally, an abscess is allowed to heal from the inside out. Thus, once drained, the wound is kept open to facilitate periodic irrigation, continued drainage and promote proper healing. Large abscesses may be packed with sterile gauze, although there is some evidence to show that this can impede the healing process. (O'Malley, G. F. et al., (2009) "Routine Packing of Simple Cutaneous Abscesses is Painful and Probably Unnecessary," Academic Emergency Medicine, 16(5): 470-473.)

If the area does not drain sufficiently and/or irrigation is not performed adequately, the abscess will reform. This often happens if the wound opening or abscess incision closes too soon, or if the abscess is too deep for all of the pus to drain or be irrigated from the incision. Applying pressure to the area to force the pus to drain is not recommended since that can actually force the pus deeper into the tissues, causing further damage.

Irrigation is the most common and safest procedure for cleansing and debriding open contaminated wounds. Irrigation involves the application of sterile solutions or fluids to wounds to remove loose devitalized tissue, bacterial inoculum, blood clots, loose debris, and foreign bodies proximate to and within the depths of the wound. The two critical components of any effective wound irrigation method and/or device are: (1) the application of an adequate volume of sterile irrigation solution to the wound, and (2) the use of sufficient pressure applied in an effective dispersal pattern in the delivery of the solution to effectively remove contaminants. It is not uncommon for wounds, to require a liter or more of irrigation solution. (Mulliken, John B. (1984) "Management of Wounds," in *Emergency Medicine*, May ed., John Wiley & Sons, pp. 283-286.) It has also been demonstrated that stream pressure of a minimum of 4 pounds per square inch (psi) (and, preferably, 7 psi) is required to effectively flush or remove contaminants from a wound. See, for example, Rodeheaver, G. T. Wound Cleaning, Wound Irrigation, Wound Disinfection, In: Krasner, D., Kane, D. Chronic Wound Care. $2^{nd}$ ed. Wayne, Pa.; Health Management Publications; 1997, pp 97-108; and Bergstrom, N., Bennett, M. A., Carlson, C. E. et al. Treatment of Pressure Ulcers. Clinical Guideline No. 15. AHCPR Publication No. 95-0652. Rockville, Md. Department of Health and Human Services. Public Health Services, Agency of Health Care Policy and Research; December 1994.)

Irrigation pressure in excess of desired limits (e.g., 25 psi or greater) may actually drive bacteria and particulate matter deeper into the wound and thereby defeat the purpose of the irrigation process. High-pressure irrigation may also cause damage to healthy tissue and impede the tissue's defenses and retard healing. Thus, effective wound irrigation requires the use and application of adequate volumes of irrigation solution delivered to the wound in an effective dispersal pattern at appropriate pressures.

Unfortunately, most irrigation devices and methods are effective only on relatively shallow wounds or larger open wounds, such as burns or large open cuts. Deeper wounds, particularly those with smaller openings, such as abscesses or puncture wounds, would obtain only minimal benefit from a surface irrigation procedure. Devices currently used to cleanse deeper wounds, such as various types of syringe models, often do not have sufficient pressure, or fluid dispersion to actually debride tissues and/or cannot deliver a sufficient amount of solution to thoroughly flush out an abscess or similar wound.

More recently, an advantageous wound irrigation system has been developed whereby a dispersed stream of irrigation fluid is easily and effectively applied to wounds. This system is described at, for example, U.S. Pat. Nos. 5,830,197 and 6,468,253 and International Patent Applications WO 00/15279 and WO 02/007799. A specific embodiment of this system is also disclosed in U.S. Design Pat. D588,692 and D556,595.

Although the use of the dispersed stream is highly advantageous for cleansing wounds, it has been determined that the shape and size of the nozzles delivering the irrigation fluid can be improved for use in irrigating puncture wounds, abscesses, and similar deep tissue wounds.

BRIEF SUMMARY OF THE INVENTION

The subject invention successfully addresses the above described disadvantages associated with the previously known abscess irrigation devices and methods, and provides certain attributes and advantages, which have not been realized by these known devices.

In particular, the subject invention provides novel, inexpensive, and highly effective methods and devices for convenient and effective irrigation of abscesses and other deep tissue wounds. In one embodiment, the subject invention provides a discharge apparatus (LT SplatterGuard™) for a reservoir housing containing irrigation solution, wherein the discharge apparatus has one or more specifically designed nozzles for penetration into an abscess capsule or other wound, and through which a sufficient volume of the irrigation solution can pass at an appropriate pressure for effective cleansing and debriding. Surrounding the nozzle can be a backsplash shield that reduces or eliminates backsplash and/or aerosol hazards to healthcare providers when expressing irrigation solution from the reservoir.

In particular embodiments, the device has a slender, elongated nozzle with a plurality of outlet ports. In a further embodiment, the nozzle and plurality of outlet ports are specifically designed to reduce loss of pressure as the irrigation fluid leaves the reservoir housing. There are three elements of the design that can be particularly important—the shape of the nozzle, the length of the nozzle, and the configuration of the plurality of outlet ports. In a specific embodiment, the nozzle is generally slender, elongated, and comprises several passageways or outlet ports. In a further embodiment, the nozzle is surrounding by a backsplash shield.

In a further particular embodiment, the reservoir housing, upon which a discharge apparatus can be either permanently or detachably affixed, is compressible (e.g., plastic bottles in which saline or other solutions are presently available). The operator (i.e., medical or health care professional or other person) using the subject device and providing wound irrigation therapy can insert the end of the nozzle into a wound opening, such as an abscess incision, or puncture opening and easily compress the reservoir housing to force the irrigation solution through the outlet ports of the discharge apparatus under sufficient pressure to dislodge dirt, debris, devitalized tissue, or other particles, including microorganisms, e.g., pathogenic bacteria. Continued compression fills and flushes the wound or abscess cavity, removing the debris and leaving a clean and debrided cavity less susceptible to infection and more amenable to the normal healing process.

Specifically exemplified herein is the use of a single, elongated nozzle, with multiple outlet ports to achieve optimum dispersal, pressure, and volume of the stream of irrigation solution.

In a further embodiment, the subject invention provides a laceration tray that has items conveniently provided for treating wounds.

In yet another embodiment, the subject invention provides a drain pan for collection of fluids.

In still another embodiment, the subject invention provides a sterile product for use in an operating room environment.

In another embodiment, the subject invention provides a pressurized irrigation assembly comprising: irrigation solution; a reservoir housing that contains the irrigation solution; a discharge apparatus having a specifically designed nozzle with multiple outlet ports through which a sufficient volume of the irrigation solution can pass at an appropriate pressure; and a means for creating pressure for the generation of dispersed streams through the outlet ports in the nozzle to cleanse and flush abscesses or other deep tissue wounds.

The devices and methods disclosed herein provide an easy to use, economical wound irrigation system that is capable of delivering adequate volumes of irrigation solution (without refilling the reservoir) in a dispersed stream under sufficient pressure to effectively cleanse and flush the wound, thereby reducing the presence of infection and the possibility of recurrence of the abscess.

An operator, without assistance, can easily penetrate a wound opening with the nozzle and direct and control the application of irrigation solution into the wound or abscess with one hand. This can leave the other hand free for other activities, such as separation of the wound opening, compression of the wound site to expel the solution and other material carried therewith, and to further facilitate irrigation of the wound interior and/or exterior.

BRIEF SUMMARY OF THE FIGURES

In order that a more precise understanding of the above recited invention can be obtained, a more particular description of the invention, briefly described above, will be rendered by reference to specific embodiments thereof that are illustrated in the appended drawings. It should be understood that the drawings presented herein may not be drawn to scale and that any reference to dimensions in the drawings or the following description are specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which.

DETAILED DESCRIPTION OF THE INVENTION

Figure 1:
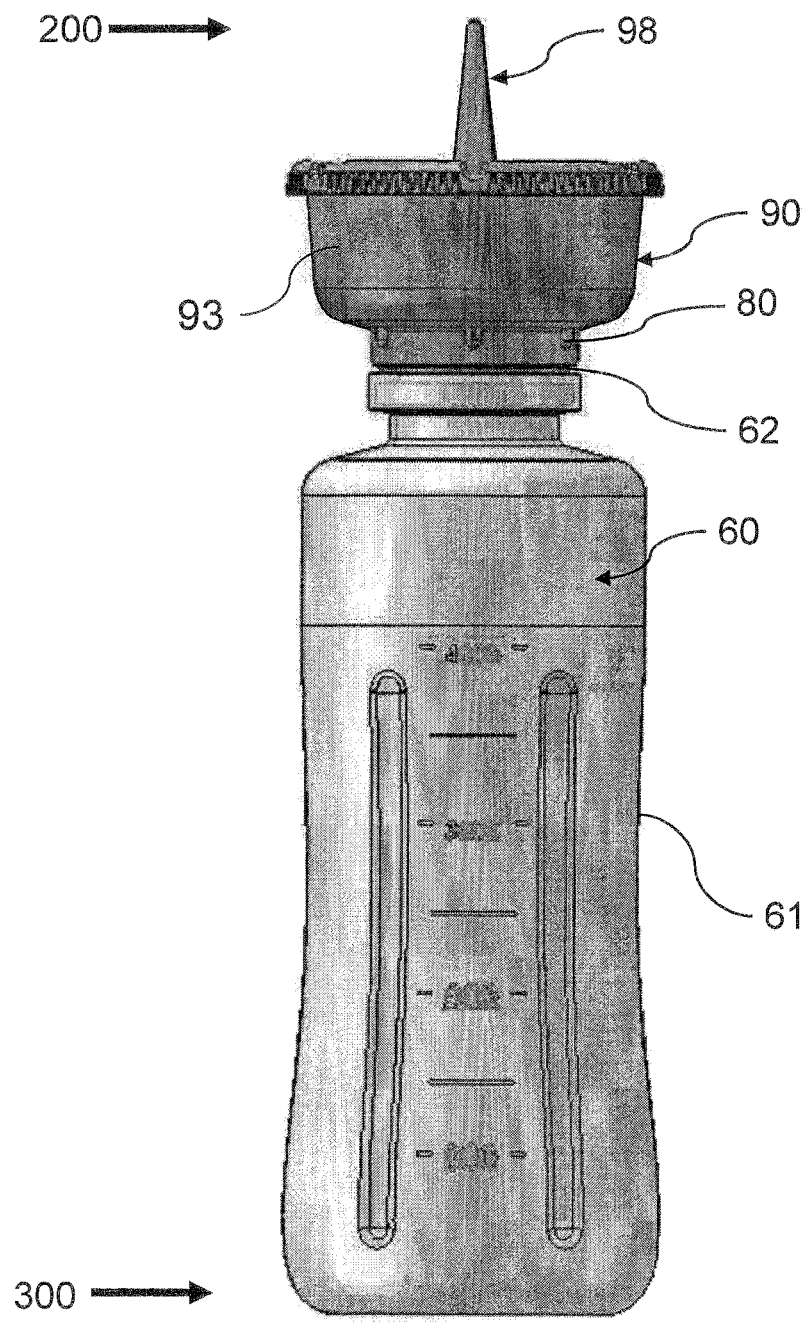
FIG. 1 shows a front elevation view of one embodiment of an abscess irrigation device of the subject invention that includes a compressible reservoir housing, and a discharge apparatus having a nozzle for directing a pressurized stream of irrigation solution into an abscess.

The subject invention provides novel, convenient, inexpensive, and effective abscess irrigation devices that can include a reservoir housing and a discharge apparatus having a single nozzle with one or more outlet ports for irrigation of an abscess. The subject invention also provides methods of use for the device.

The materials and methods of the subject invention make it possible to conveniently and easily direct one or more streams of irrigation fluid into an abscess with the stream(s) having an appropriate volume, pressure, and dispersal pattern. Under optimal circumstances, the abscess irrigation devices and methods of the subject invention are utilized by trained medical technicians; however, because of the simplicity and convenience of the devices of the subject invention, they can be used to greatly enhance the effectiveness of abscess irrigation regardless of the training level of the operator performing the irrigation.

The subject invention is particularly useful in the field of wound irrigation, in particular abscess irrigation. However, a person with skill in the art will be able to recognize numerous other uses that would be applicable to the devices and methods of the subject invention. While the subject application describes a use for irrigation of abscesses and/or abscess pockets, other uses, and resulting modifications therefor, that are apparent to a person with skill in the art having benefit of the subject disclosure are contemplated to be within the scope of the present invention.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

Finally, the various components referred to herein are described with reference to the "proximal end" and/or "distal end." As used herein, the proximal end 200 is that end of the device that, in use, would be placed nearest to or within an abscess. Conversely, the distal end 300 of the device is that end that, in use, is furthest from an abscess and from the proximal end.

In one embodiment, the nozzle and outlet ports of the subject invention are designed to expel irrigation fluid(s) into an abscess pocket. In a particular embodiment, the nozzle and outlet ports of the current invention are specifically designed to reduce pressure loss as the irrigation fluid leaves the reservoir housing. The outlet ports can disperse fluid in a variety of directions. In one embodiment, the outlet ports disperse fluid in a single direction, such as, for example, straight out from the nozzle tip. In an alternative embodiment, the outlet ports of the nozzle are specifically designed to provide a wide dispersal pattern as the irrigation fluid leaves the reservoir housing. Thus, there are three elements of the design that are particularly important—the shape of the nozzle, the length of the nozzle, and the configuration of the one or more outlet ports. Preferably, the nozzle is elongated and comprises a single shaped passageway, or bore, that leads to the one or more outlet ports for dispersal of the irrigation fluid.

In one embodiment, the nozzle acts similar to a jet through which irrigation fluid is forced, under pressure, to achieve velocities and pressures appropriate for efficient abscess irrigation. The nozzle and outlet ports are designed to reduce friction and turbulence and facilitate achieving sufficient irrigation pressures with minimal operator effort.

With reference to the attached figures, which show certain embodiments of the subject invention, it can be seen that embodiments of the subject invention include a discharge apparatus 80 for attachment to a reservoir housing, as shown, for example, in FIG. 1. In a more particular embodiment, the discharge apparatus includes a nozzle 98 attached to, or attachable to, the discharge apparatus and a backsplash shield 90 either attached to or attachable to the reservoir housing 60. The nozzle 98 can further have at least one inlet port 102 and one or more outlet ports 104.

Figure 3:
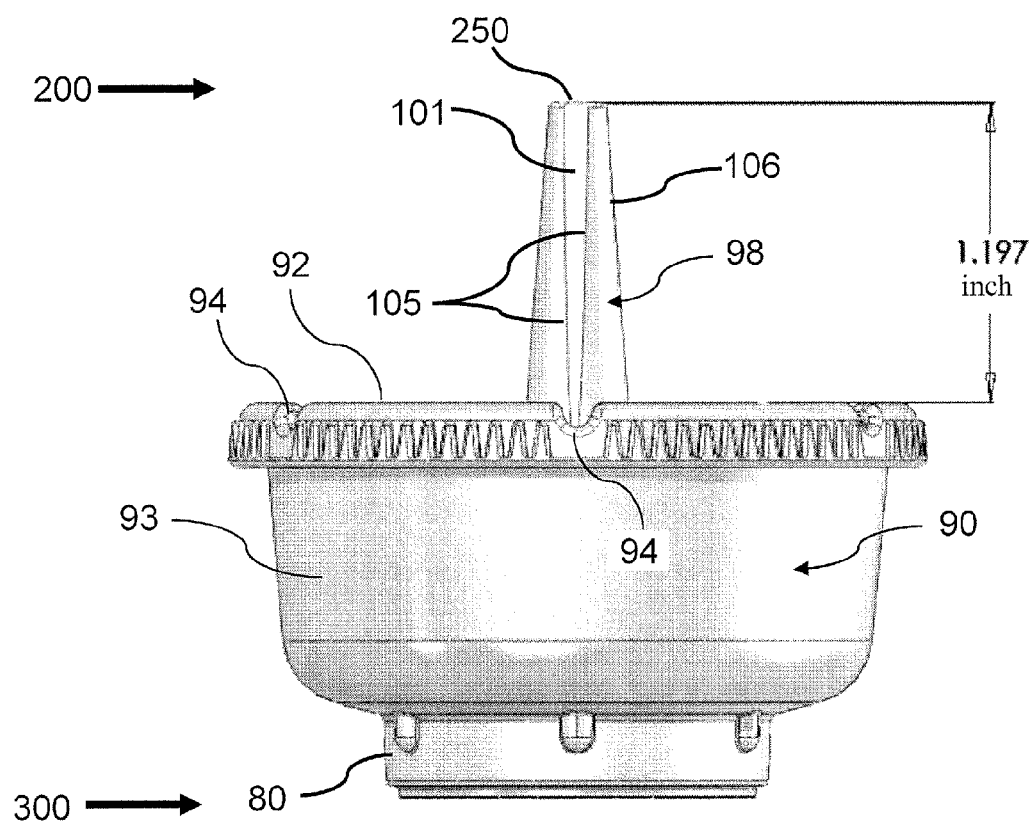
FIG. 3 shows a front elevation view of an embodiment of the discharge apparatus of subject invention.
Figure 4:
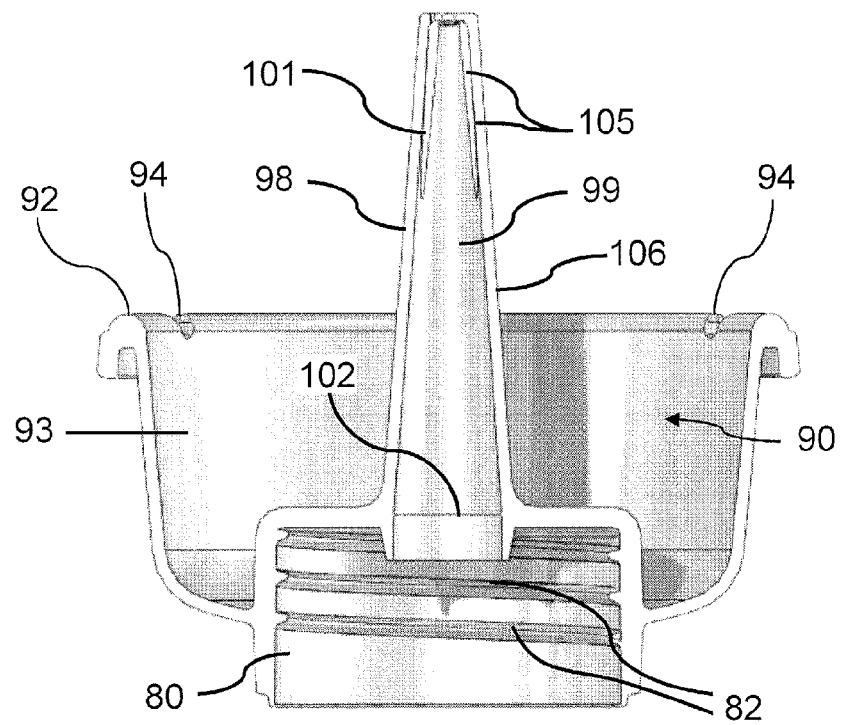
FIG. 4 shows a cross-sectional view of the embodiment in FIG. 3.

In one embodiment, the nozzle 98 defines a bore 99 that delivers a stream of irrigation fluid from the inside to the outside of the reservoir housing 60. FIGS. 3 and 4 illustrate one embodiment of the subject invention. In accordance with this embodiment, the length of the nozzle 98 from the inlet port 102 to the outlet ports 104 is between approximately 1.5 inches and approximately 2.5 inches. In a more particular embodiment, the length of the nozzle from the inlet port 102 to the outlet ports 104 is between approximately 1.8 inches and approximately 2.0 inches. In a specific embodiment, the nozzle extends between approximately 1.0 inches and 1.3 inches beyond the rim 92 of the backsplash shield 90. In a more specific embodiment, the proximal end of the nozzle extends about 1.2 inches beyond the rim 92 of the backsplash shield.

Figure 17:
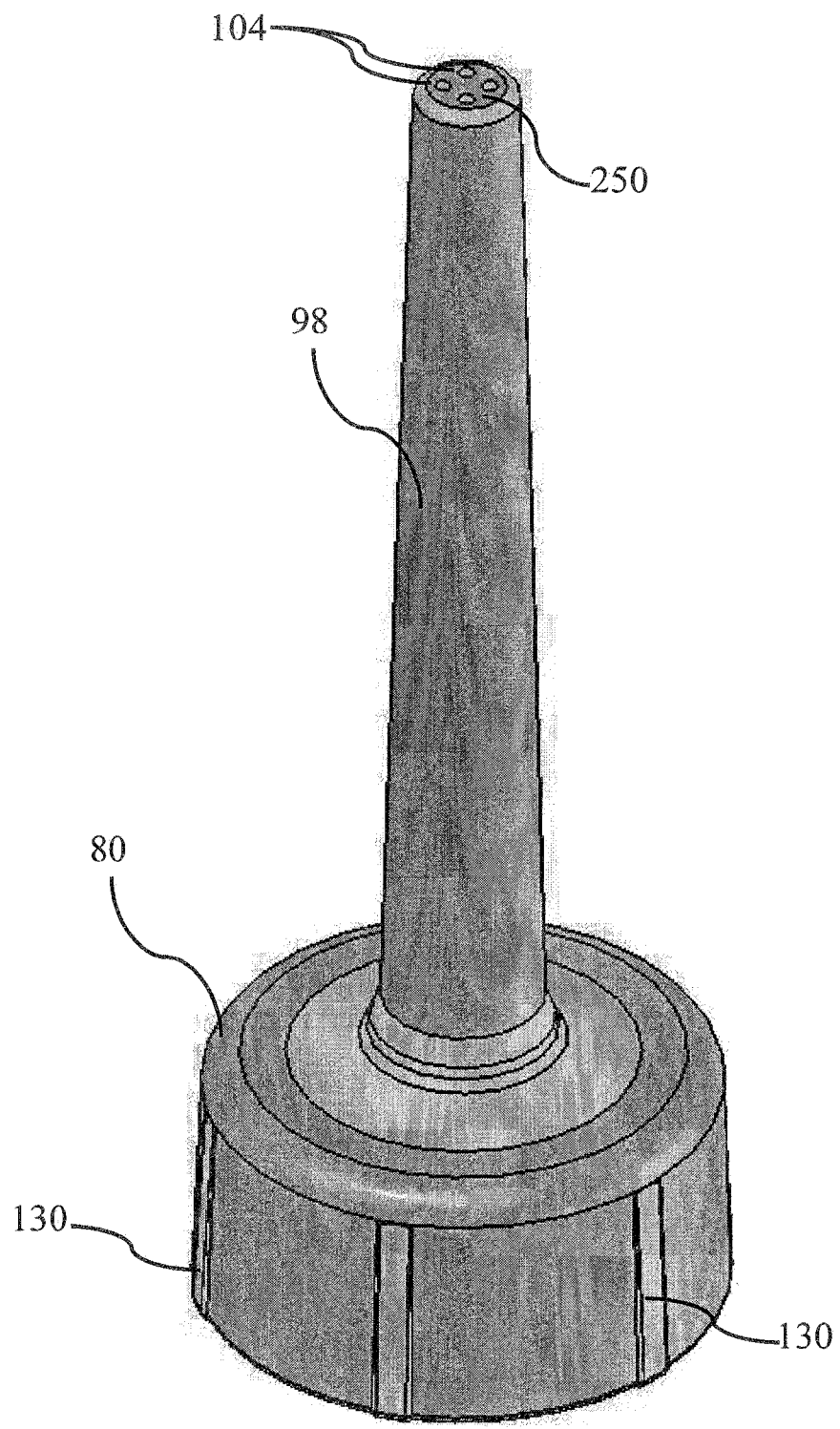
FIG. 17 illustrates an alternative embodiment wherein the discharge apparatus comprises an elongated nozzle with four outlet ports, but does not include a backsplash shield.
Figure 18:
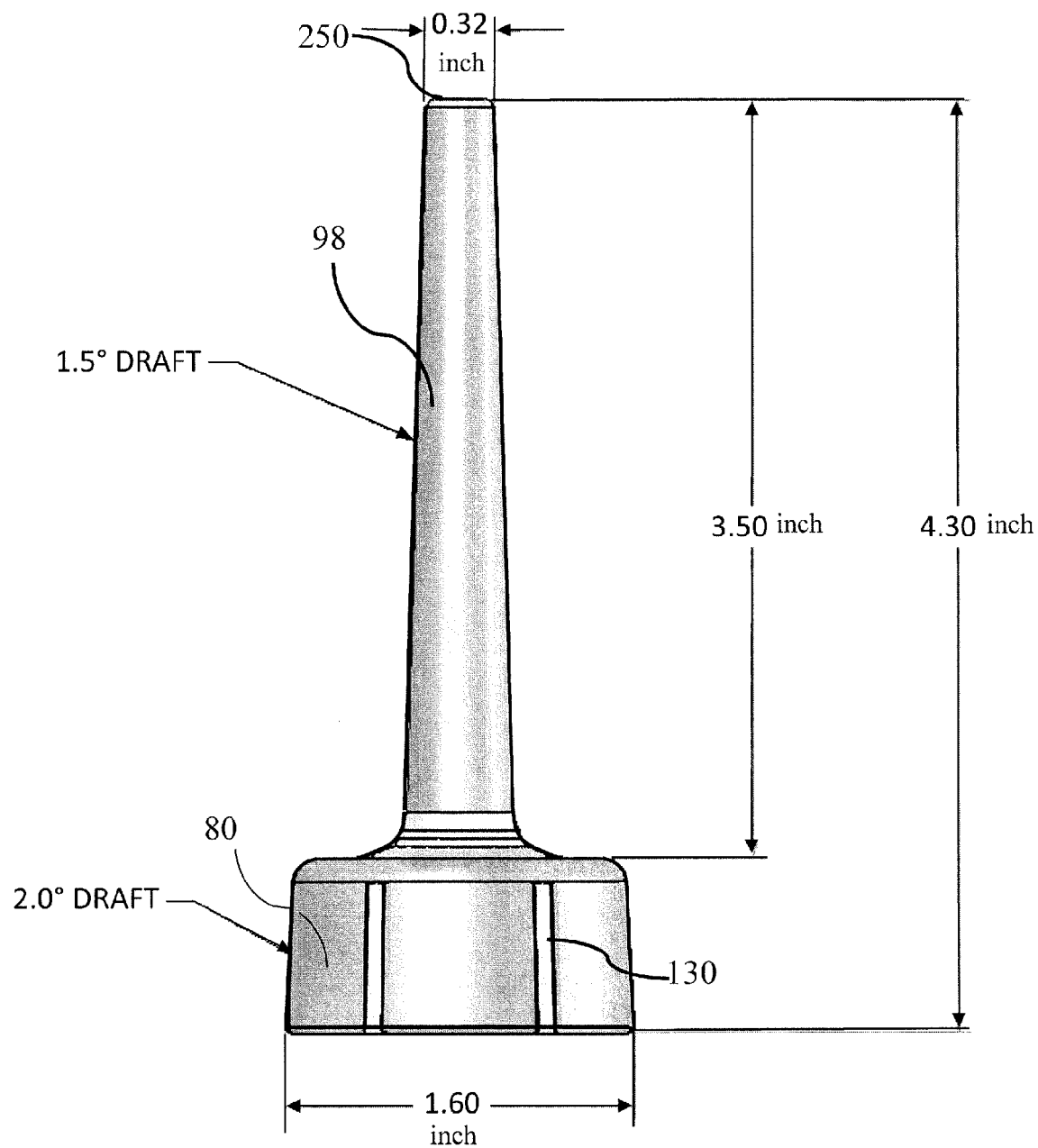
FIG. 18 is a side plan view of an alternative embodiment of the discharge apparatus, including specific dimensions.

In an alternative embodiment, an example of which is shown in FIGS. 17 and 18, the total length of the discharge apparatus and nozzle is between approximately 3 inches and 4 inches. In a more specific embodiment, the total length of the discharge apparatus and nozzle is approximately 4.3 inches. In a still more particular embodiment, the length of the nozzle is approximately 3.5 inches and the length of the discharge apparatus is approximately 0.8 inches.

Figure 8:
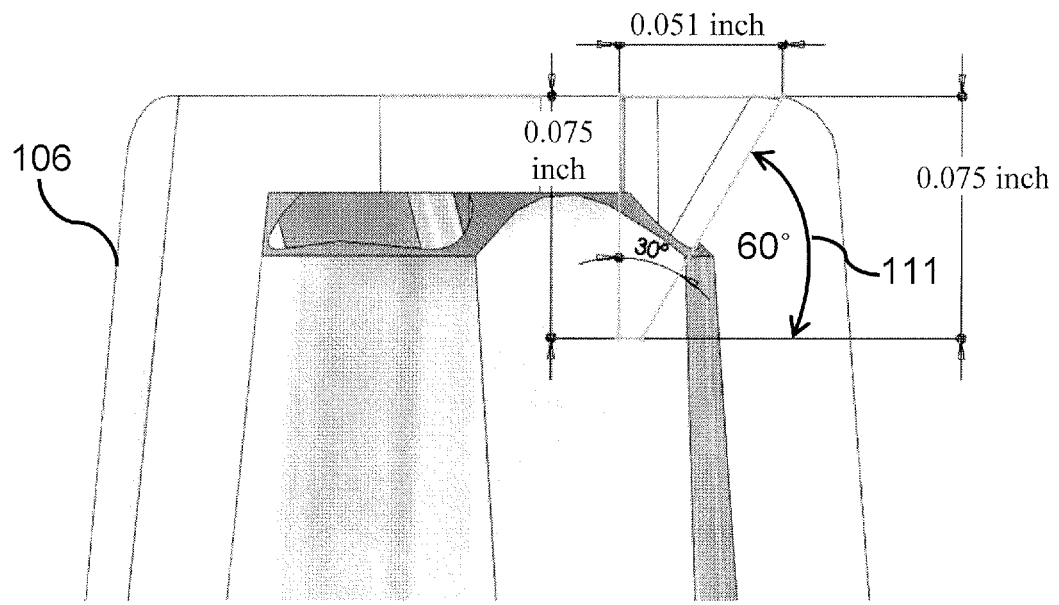
FIG. 8 shows an enlarged sectional side view of the nozzle of FIG. 7.

In certain embodiments of the invention, the nozzle is a "shaped" nozzle that defines the passageway through which the fluid travels (see FIGS. 4 and 8). In one embodiment, the passageway extends through the length of the nozzle and is defined by the bore 99, which narrows as it approaches the outlet ports 104. The passageway of the nozzle can limit the generation of turbulence in the irrigation fluid as it passes through the nozzle(s) during operation of the abscess irrigation device of the subject invention. Therefore, fluid passing through the nozzle experiences laminar flow (or at least a reduction in turbulence) as it passes through and exits the nozzle through the output ports. Thus, as used herein, reference to the "shaped" passageway refers to a nozzle with a passageway where the cross-sectional area of the inlet port 102 is greater than the cross-sectional area of the one or more outlet ports 104. This shaped nozzle has been found to be particularly advantageous for achieving desired irrigation fluid pressures and velocities according to embodiments of the subject invention.

In a specific embodiment, the nozzle bore 99 is defined by a funnel shape or conical shape where the nozzle cross-section decreases from an upstream wider end at or near the inlet port 102 to the downstream end at or near the outlet ports 104.

Figure 2:
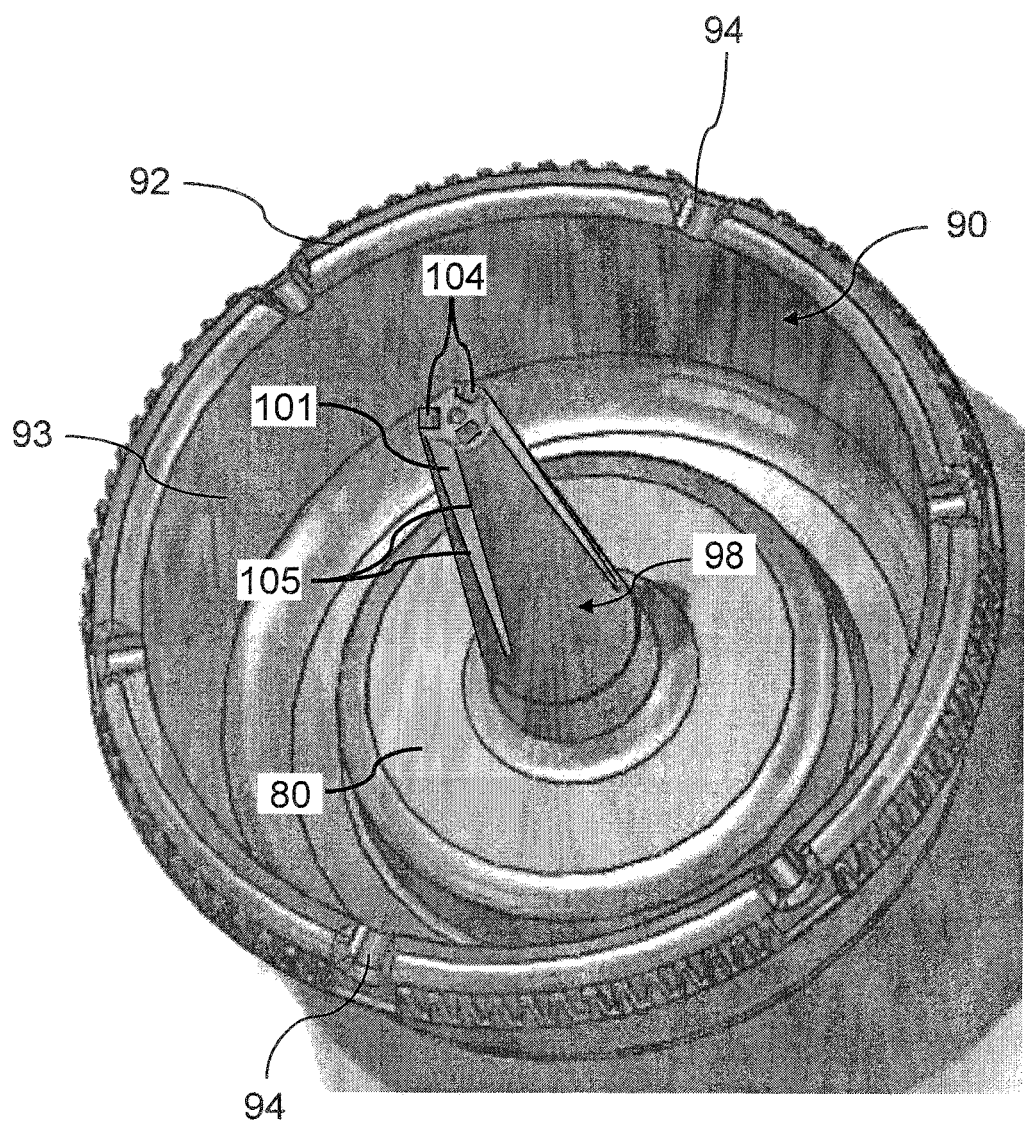
FIG. 2 shows an enlarged perspective view of an embodiment of the discharge apparatus of the abscess irritation device of the subject invention.

FIGS. 2, 3, and 4 show a specific embodiment of the elongated, shaped nozzle of the subject invention. In this embodiment, the nozzle extends approximately 1.2 inches above the rim 92 of the backsplash shield 90.

As would be appreciated by a person skilled in the art having the benefit of the current disclosure, the nozzle of the subject invention can be formed from and/or extend from the material of the discharge apparatus 80. Thus, for example, if the discharge apparatus is formed of a plastic material, the nozzle can be formed of and extend proximally from the same material of the discharge apparatus, such that the bore extends through the discharge apparatus. Alternatively, the nozzle can be formed as a separate piece, and even a different material than the discharge apparatus, and can be attached to the discharge apparatus. In this alternative embodiment, the discharge apparatus has an opening that is contiguous with the bore 99, when the nozzle is attached thereto.

The embodiments disclosed herein are specifically designed to permit irrigation of an abscess. Thus, the elongated nozzle permits the proximal end to be placed within close proximity to the abscess opening. However, it can be more beneficial if the proximal end is inserted within the abscess opening, e.g., within the drainage incision. This can allow the force of the irrigation fluid to debride affected tissues and better cleanse the interior of the abscess pocket, to promote better healing from the inside out. To assist with insertion of the nozzle into an abscess opening, the nozzle can be narrow or slender in diameter for easy insertion and to prevent damage to surrounding tissue. In one embodiment the nozzle is an elongated tubular-like structure having an exterior diameter of between approximately 0.125 inches and approximately 0.375 inches. In a more particular embodiment, the nozzle has an exterior diameter of between approximately 0.1875 inches and approximately 0.3125 inches. In a specific embodiment, the nozzle has an exterior diameter of approximately 0.25 inches. The circumferential shape of the nozzle can have various forms, such as, for example, circular, oval, triangular, square, or any other polygonal shape suitable for the intended purposes. In a specific embodiment, illustrated in the attached figures, the circumferential shape is circular or approximately circular.

As mentioned above, the interior bore 99 of the nozzle defines a passage, which is, in general, a conical shaped passage, narrowing towards the one or more outlet ports 104, which, for the embodiments disclosed herein, are located at the proximal 200 end of the nozzle. In a particular embodiment, the nozzle conforms to the shape of the passage by also tapering towards the proximal end. FIG. 4 illustrates an example of this embodiment, wherein the bore 99 and the nozzle 98 are similar or identical in shape. The tapering of the nozzle can vary and does not necessarily have to conform precisely to the tapering of the bore 99. In one embodiment, the proximal end of the nozzle has an exterior diameter of between approximately 0.125 inches and approximately 0.375 inches. In a more particular embodiment, the proximal end of the nozzle has an exterior diameter of between approximately 0.19 inches and approximately 0.32 inches. In a specific embodiment, the proximal end of the nozzle has an exterior diameter of approximately 0.25 inches.

The tapering of the nozzle can be accomplished by a variety of techniques and methods known to those with skill in the art. For example, the nozzle can taper distally in stepwise progressions, wherein distinct, pre-determined sections of the nozzle have successively larger diameters, similar to a telescope. In a more preferable embodiment, the tapering of the nozzle is a gradual narrowing from the distal to the proximal end, providing a smooth exterior surface 106 with minimal or no ridges, bumps, or other protrusions. This smooth tapering can be beneficial in preventing pain or additional tissue damage when the nozzle is inserted into an abscess opening.

The degree of taper of the nozzle can vary from a slight increase in diameter from the proximal to the distal end to a more extreme increase in diameter from the proximal to the distal end. In one embodiment, the tapering of the nozzle results in a distal nozzle exterior diameter of between approximately 0.50 inches to approximately 0.75 inches. In a more particular embodiment, the tapering of the nozzle results in a distal nozzle exterior diameter of between approximately 0.56 inches to approximately 0.69 inches. In a specific embodiment, the tapering of the nozzle results in a distal nozzle exterior diameter of approximately 0.625 inches.

Figure 19:
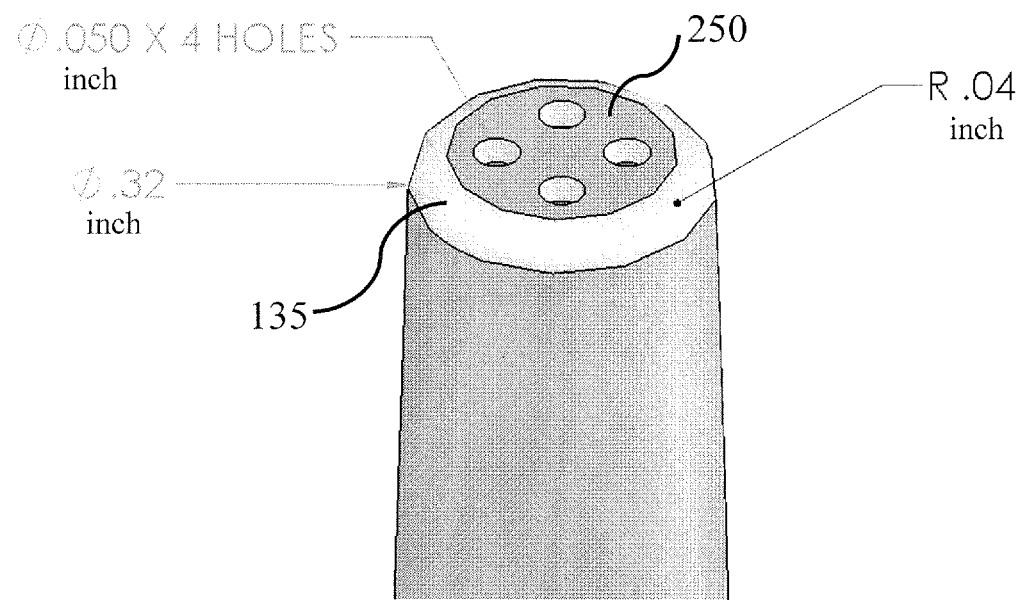
FIG. 19 is an enlarged view of the alternative embodiment shown in FIG. 18, specifically illustrating the nozzle end and details of an alternative embodiment of the outlet ports. Specifically illustrated in this embodiment are outlet ports having straight, parallel sides that direct fluid in a generally straight line directly from the nozzle tip.

For the irrigation fluid and other material to be washed out of the abscess pocket, it is important that the fluid be able to exit the abscess pocket. This can be accomplished by providing at least two abscess openings. However, in most instances, there is a single abscess drainage opening. Thus, for proper irrigation, it can be important that the nozzle, when inserted, not plug or otherwise close-off the entire abscess opening. To prevent blockage of the drainage opening, the nozzle can be configured to have as small a diameter as possible. FIGS. 17-19 illustrate one embodiment wherein the diameter of the nozzle at the proximal face 250 is approximately 0.32 inches and the taper draft is approximately 1.5°. This can provide a nozzle having a generally slim overall length, that can be inserted into an abscess pocket without blocking the opening.

Figure 5:
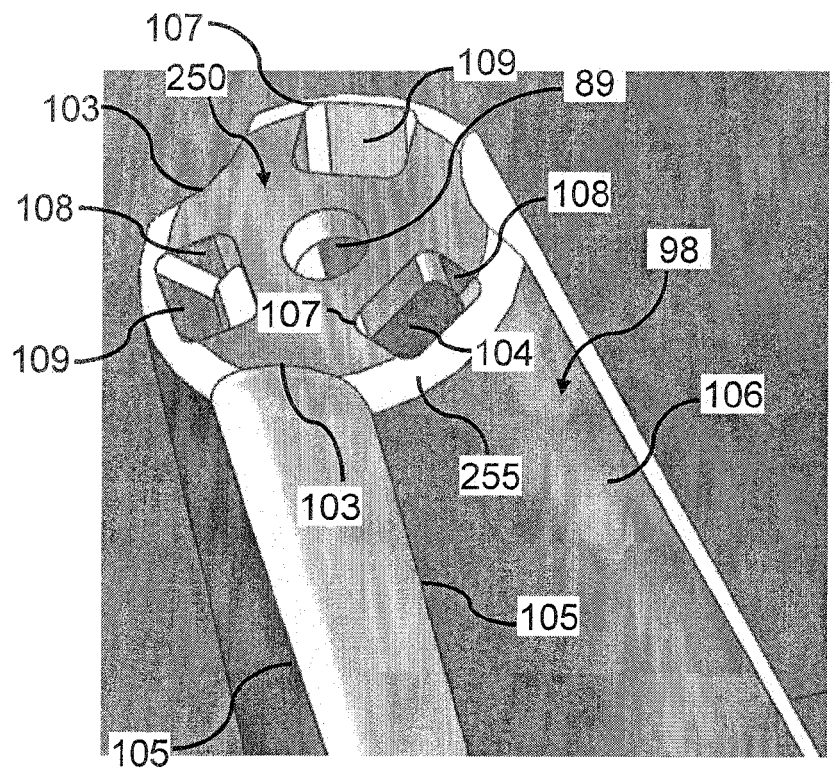
FIG. 5 shows an enlarged right-side perspective view of an embodiment of the nozzle, particularly the outlet ports, and gutters of a specific embodiment of the subject invention.
Figure 6:
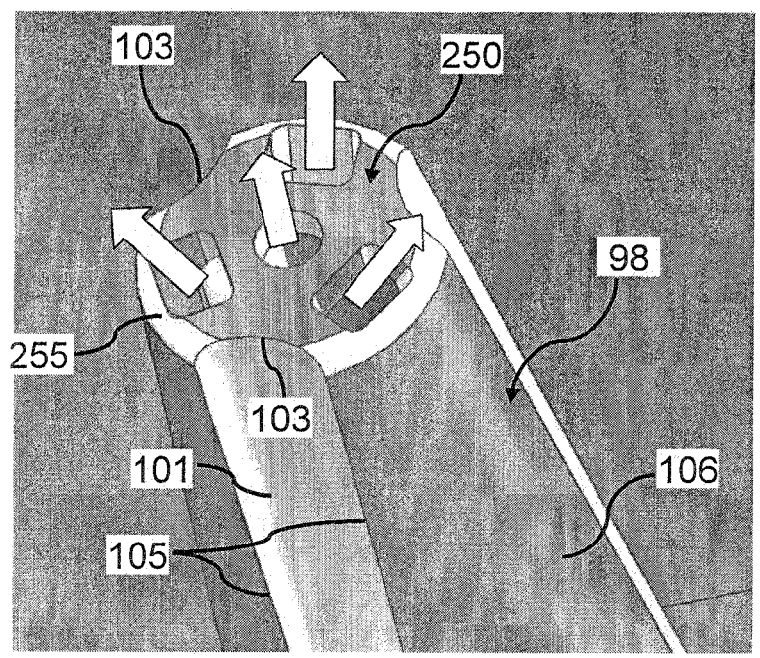
FIG. 6 shows the enlarged perspective view of FIG. 5A with arrows indicating the direction of fluid flow from the nozzle outlet ports.

In another embodiment, the nozzle is configured with one or more longitudinal gutters 101 that extend from the proximal face 250 towards the distal end 300 of the nozzle, such as shown, for example, in FIGS. 2 and 4. In a particular embodiment, the nozzle employs three gutters placed equidistantly around the perimeter of the nozzle, an example of which is shown in FIGS. 5 and 6.

The length of a gutter can vary depending upon any of a variety of factors known to those with skill in the art. In one embodiment, the gutters 101 extend along the entire length of the nozzle. Alternatively, the gutters 101 can extend from the proximal end and have a length that is less than the length of the nozzle. In a particular embodiment, the gutters 101 extend from the proximal end and terminate at about the rim 92 of an attached backsplash shield, for example, as shown in FIG. 3. In yet another embodiment, the gutters 101 extend below the rim 92, but terminate before reaching the distal end of the nozzle. In still another embodiment, the gutters 101 terminate above the rim. A person with skill in the art would be able to determine an appropriate length for a gutter. Any and all such alternatives are contemplated to be within the scope of the embodiments of the subject invention.

In general, a glitter 101 can be a groove, channel, or other similar indented area on the exterior surface 106 of the nozzle. When the nozzle is inserted into an abscess opening, the gutters can provide gaps between the nozzle and the abscess opening that permit backflow of irrigation fluid, air, and other material to exit the abscess pocket during the irrigation process. As such, gutters can have any of a variety of configurations or dimensions suitable for maintaining such gaps. In one embodiment, a gutter is simply a flattened area or a straight indentation longitudinally down one or more sides of the nozzle, such as shown, for example, in FIG. 9. In this embodiment, the proximal edge 103 appears as a straight line, such as in the example shown in FIG. 9.

However, to encourage proper irrigation drainage, it can be important that the gutter depth be sufficient to allow rapid exiting of backflow, but not interfere with or weaken the structure of the outlet ports 104. In one embodiment, a gutter has a more curvilinear indentation that provides a larger gap without interfering with, or detrimentally weakening, the material around the outlet ports. Thus, in this embodiment, the gutter depth would be greater than that provided by a more flattened or straight sided configuration. Further, the proximal edge 103 would appear more curved, such as seen, for example, in FIGS. 5, 6, and 7. The curved configuration beneficially allows the gutters to extend into the area between two or more outlet ports 104, providing the benefit of a larger drainage gap without compromising the integrity of the outlet ports.

The depth of a gutter can vary as well. For example, they can employ a consistent depth from the proximal to the distal end. Alternatively, a gutter can have a more tapered depth, such that the distal end is gradually shallower than the proximal end, which can contribute to a smoother, tapered distal end, an example of which is shown in FIG. 2. Because the nozzle can be inserted into an abscess opening, it can be beneficial for it to have a smooth exterior surface 106, with minimal or no ridges, bumps, or other protrusions. A smooth exterior surface can also be beneficial in preventing pain or additional tissue damage when the nozzle is inserted into an abscess opening. In this regard, the configuration of the gutters can be such that a smooth, uniform, exterior surface is achieved as much as possible. In a particular embodiment, the gutters have a curvilinear configuration that becomes shallower and tapers towards the distal end. This embodiment provides gutters of sufficient depth for drainage and a generally smooth exterior surface to the nozzle. FIGS. 2 and 4 illustrate an example of this embodiment.

In an alternative embodiment, a gutter maintains a consistent or substantially consistent depth from the proximal end to the point of termination towards the distal end. In this alternative embodiment, the distal end of the gutter would not taper, but rather, would terminate as an indented or ridge-like surface 85, as seen, for example, in FIG. 9. In a further embodiment, a gutter could maintain a consistent depth from the proximal to approximately the distal end, wherein the terminal end of a gutter could taper towards the exterior surface. Various alternative embodiments would be apparent to a person with skill in the art. Such variations are contemplated to be within the scope of the subject invention.

Depending upon the configuration of a gutter, the sides 105 of the gutters can be parallel along their, entire length or they can converge towards the distal end, or have some combination thereof. In a specific embodiment, illustrated, for example, in FIGS. 2 and 3, the gutter edges 105 converge towards the distal end, as the depth of the gutters becomes shallower, such that the distal end converges with the exterior surface 106 of the nozzle. This embodiment can provide a smoother edge for easier insertion into an opening and can further reduce or eliminate undesirable splashing as irrigation fluid exits the abscess.

The dimensions, including, but not limited to, the depth and length of a gutter utilized with the embodiments of the subject invention can vary depending upon a variety of factors. These can include, but are not limited to, the type of material utilized for the nozzle, the thickness of the material, the configuration of the outlet ports, and other factors that would be known to those with skill in the art. Thus, the determination of an appropriate gutter depth is within the competence of a person skilled in the art, as are its dimensions for the intended purpose. Such variations are contemplated to be within the scope of the embodiments of the subject invention.

As mentioned above, most currently used irrigation devices and methods are effective only on relatively shallow wounds or on larger open wounds, such as burns or large open cuts. Usually various types of syringe models are utilized for irrigation. A typical syringe used for irrigation, as is well known in the art, is often a 16 or 18 gauge syringe. However, the disadvantage of using syringes, and similar devices, is that they seldom provide sufficient pressure and/or fluid dispersion to actually debride tissues and usually cannot deliver a sufficient amount of solution to thoroughly flush out an abscess or similar type of wound.

A particularly advantageous embodiment of the subject invention is the unique design of the output ports 104 within the nozzle 98 that provide an easy and convenient method of creating a widely dispersed stream of irrigation solution, having the appropriate volume, pressure and dispersal pattern to ensure effective irrigation of an abscess pocket. As used herein, reference to a "dispersed" stream of solution means that the area from which the stream emanates, or the area that it contacts, is larger than that which can be achieved using a typical 18 gauge "single-stream" syringe for irrigation.

In one embodiment, the dispersed stream is achieved by using multiple outlet ports 104. FIGS. 17 and 19 illustrate an embodiment that utilizes multiple outlet ports. The outlet ports can act as conduits between the cylindrical bore 99 and the exterior of the nozzle 98. As such, the depth 100 of an outlet port will necessarily be determined by the thickness of the nozzle material at or about the proximal end of the nozzle. Deformation of the nozzle, particularly the proximal end of the nozzle, during the irrigation process, can be problematic, particularly if it affects the performance of the outlet ports. Therefore, it can be beneficial for the nozzle material to be of sufficient strength and/or thickness to prevent bulging, bending, extension, or any other type of undesirable deformation of the nozzle. In one embodiment, shown in FIGS. 17 and 19, the outlet ports have a diameter of approximately 0.050 inches. In another embodiment, shown for example in FIG. 8, the outlet ports have a depth of between approximately 0.07 inches and approximately 0.08 inches. In a specific embodiment, the outlet ports have a depth of approximately 0.075 inches.

Figure 7:
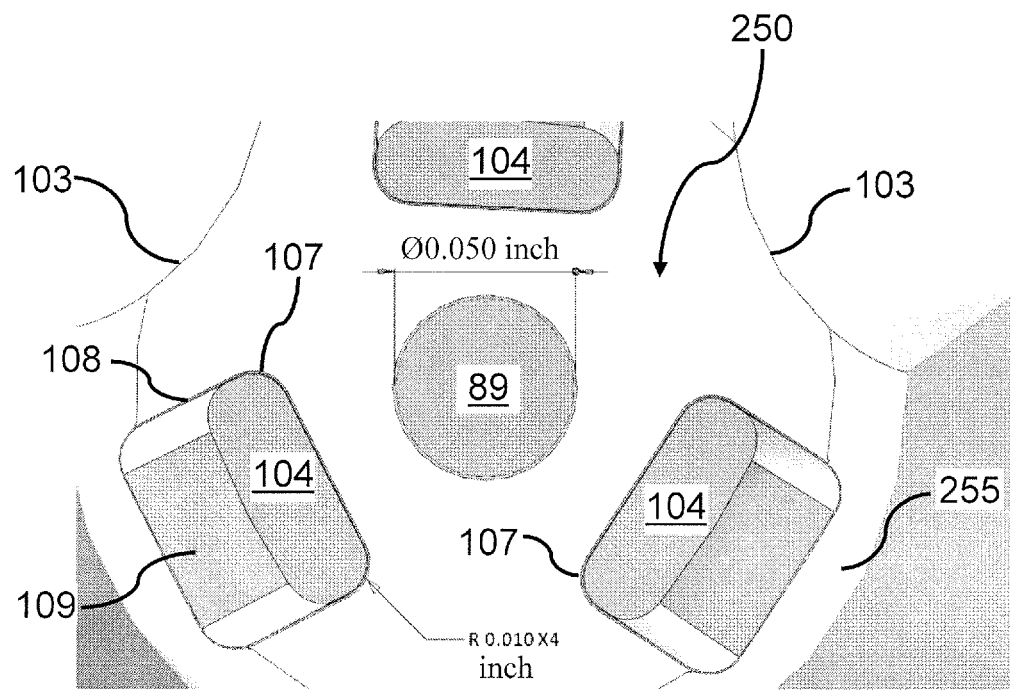
FIG. 7 shows an enlarged top plan view of one embodiment of the nozzle and outlet ports therein of the subject invention.
Figure 9:
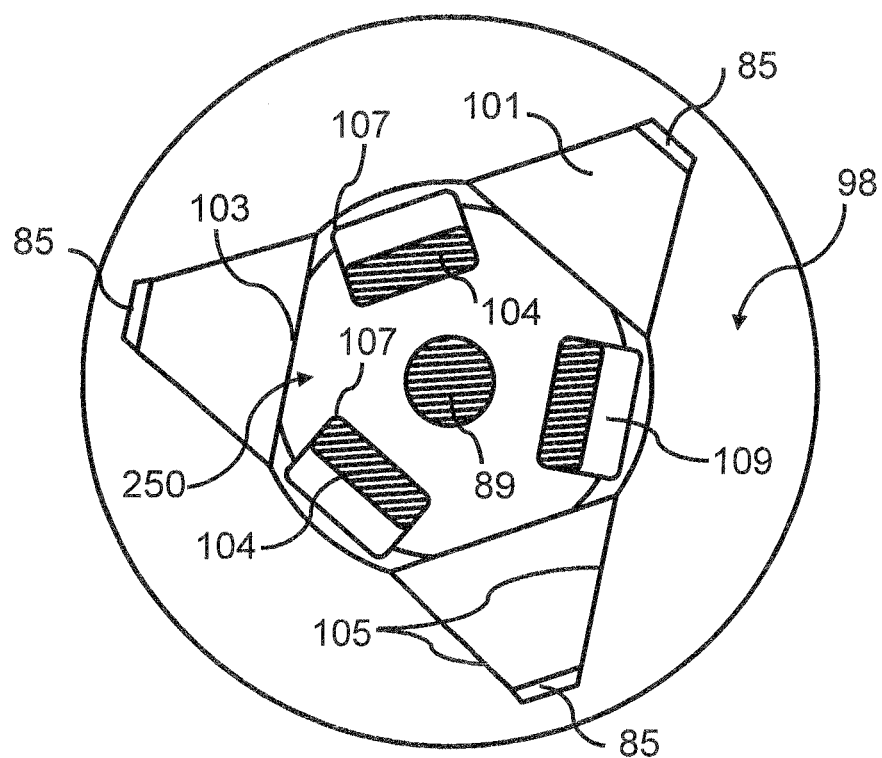
FIG. 9 shows a top plan view of the proximal end of an alternative embodiment of a nozzle having a straight-cut gutter configuration. Note that the gutters form straight edges around the proximal end of the nozzle.

The outlet ports can be configured in a variety of patterns within the nozzle, such as, for example, a circular, triangular, square, or any other polygonal shaped pattern around the proximal end of the nozzle. In one embodiment, the nozzle is configured with between approximately two and approximately six outlet ports. In a specific embodiment, the nozzle is configured with at least four outlet ports arranged in a square pattern, as shown, for example in FIGS. 17 and 19. In another specific embodiment, the nozzle is configured with four outlet ports, three of which, are arranged in a triangular pattern, for example, as shown in FIGS. 7 and 9, with a fourth outlet port in the center.

Each of the outlet ports 104 can be the same size or they can be of different sizes and various shapes. The advantage of different sized outlet ports is that the liquid can be expressed from the discharge means at different pressures. For example, an outlet port having a cross-sectional area equivalent to, or approximately equivalent to, a 16-gauge syringe needle can create a stream of fluid having about 6 p.s.i. of pressure, when the device is squeezed by a normal adult. By comparison, an outlet port having a cross-sectional area equivalent to, or approximately equivalent to, a 25-gauge syringe needle can create a stream of fluid having a maximum pressure of about 20 p.s.i. It can be beneficial for an outlet port to have a cross-sectional area less than one-eighth inch in diameter. More specifically, a cross-sectional area of between a 10 gauge syringe needle and a 30 gauge syringe needle can be most beneficial for an outlet port. In a particular embodiment, the cross-sectional area of an outlet port ranges from that equivalent to a 16-gauge syringe needle to that of a 25-gauge syringe needle.

Typically, syringes and other types of irrigation devices known in the art employ outlet ports having a circular cross-section. However, with the embodiments of the subject invention, the outlet ports can be of any of a variety of cross-sectional shapes, such as, but not limited to, oval, square, rectangular, triangular, semi-circular, or any other polygonal shape. Different shaped outlet ports can provide various types of dispersal patterns, fluid volume, stream pressure, and other variations that would be known to those with skill in the art.

In a particular embodiment, the nozzle employs outlet ports of two different cross-sectional shapes. In this embodiment, the first nozzle shape is generally circular. More specifically, this embodiment utilizes a single, circular nozzle 89 having a diameter of between approximately 0.04 inches and approximately 0.06 inches. In a still more specific embodiment, a single, circular nozzle having a diameter of 0.05 inches is used. Yet more specifically, the single circular nozzle is centrally located at the proximal end of the nozzle and directs irrigation solution in a direction that is generally collinear with the bore. FIG. 7 provides an example of such a circular outlet port utilized with the herein described nozzle embodiments.

The second type of outlet port utilized with the nozzle embodiments disclosed herein has a generally rectangular shape. This type of outlet port can provide a wider dispersal pattern and maintain sufficient fluid flow and pressure for irrigation. In one embodiment, the rectangular outlet port has a width side 108 of between approximately 0.04 inches and approximately 0.06 inches and a length side 109 of between approximately 0.05 inches and approximately 0.07 inches. In a specific embodiment, the rectangular outlet port has a width of approximately 0.05 inches and a length of approximately 0.07 inches.

It is well-known in fluid dynamics that intersecting surfaces create stagnation points where fluid flow is reduced as it approaches the vertex of the surfaces. In other words, as fluid flows through pipes or orifices, pressure is reduced nearer the point where two surfaces intersect, i.e., in corners. The area of stagnation increases as the angle of intersection decreases. Thus, to maximize fluid flow, it can be beneficial to reduce or eliminate stagnation points.

In addition, to maximize the benefits of the irrigation process, it can be important to ensure that all of the fluid is expressed at a sufficient pressure to debride tissues, pus and debris, allowing it to be carried away. Therefore, to reduce the potential of stagnation points that can occur with rectangular outlet ports, the intersections of the width side 108 and the length side 109, that is the corners 107, of the outlet ports can be rounded, curved or otherwise modified to increase the vertex angle. In one embodiment, the corners of the rectangular outlet ports have a radius of between approximately 0.005 inches and approximately 0.02 inches. In a specific embodiment, the corners of the rectangular outlet ports have a radius of approximately 0.01 inches. FIGS. 7 and 8 provide an example of this embodiment. In a more specific embodiment, the nozzle 98 includes at least three rectangular outlet ports arranged equidistantly around, and exiting at or about, the proximal end of the nozzle. In a still more specific embodiment, the rectangular outlet ports are arranged with their length side 109 nearer the exterior surface 106. As mentioned above, the one or more gutters 101 can be positioned between the outlet ports, as shown for example, in FIG. 5.

Figure 10:
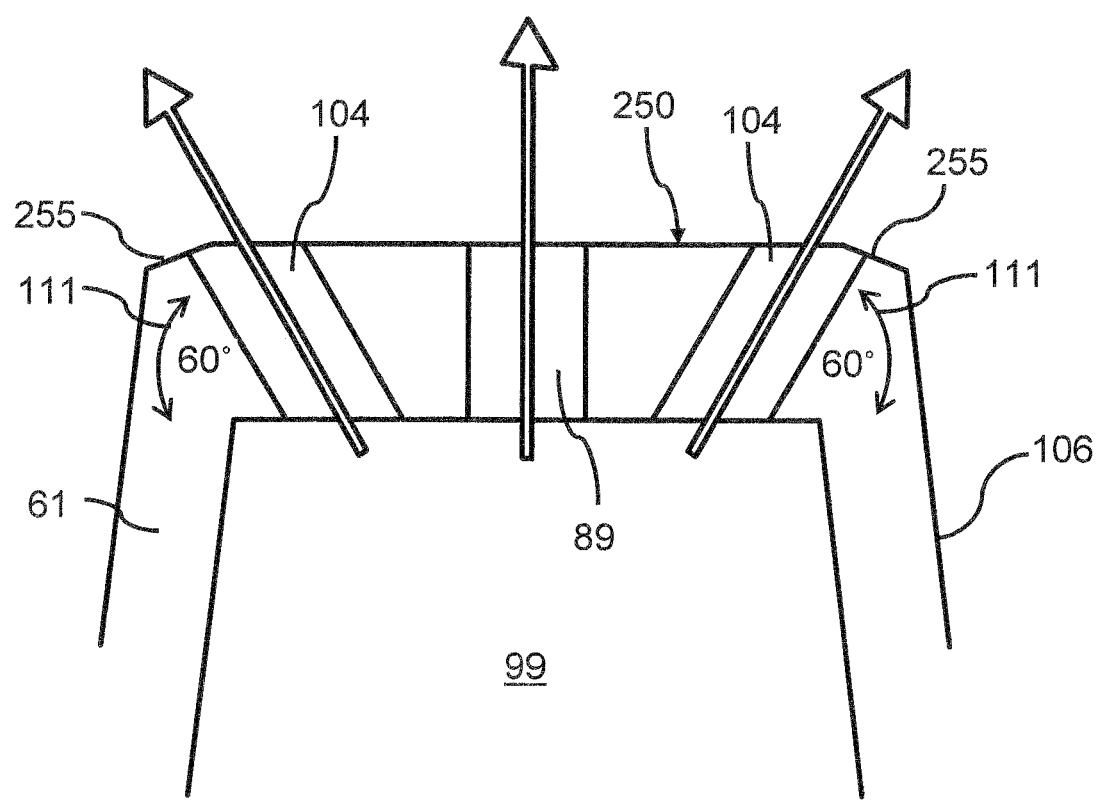
FIG. 10 shows a side cross-sectional view of an embodiment of the invention, wherein the outlet ports have a 60° angle of inclination.

Equally important can be the direction, or angle of inclination 111, of the outlet ports 104, which can determine the dispersal pattern of irrigation material. Parallel outlet ports provide multiple streams of irrigation material flowing in the same direction and usually collinear with the direction of the cylindrical bore 99. By changing the angle of inclination of one or more outlet ports, irrigation material can be directed in different directions, i.e., non-collinear with the cylindrical bore. As mentioned above, the depth 100 of the outlet ports can be determined by the thickness of the material at or about the proximal end of the nozzle. Thus, the angle of inclination 111 can be correlated to the depth 100 of the outlet port, as shown, for example, in FIGS. 8 and 10. Different outlet ports can have different angles of inclination or they can each have the same angle of inclination. In one embodiment, illustrated by way of example in FIGS. 8 and 10, the angle of inclination directs irrigation material outward from the center of the nozzle to provide a wider dispersal pattern. This permits the irrigation material to contact a larger surface area. In a further embodiment, the nozzle includes multiple outlet ports, wherein at least one has an angle of inclination that directs irrigation material away from the center of the nozzle. In a particular embodiment, the nozzle has at least three outlet ports having an angle of inclination that directs irrigation solution in one or more directions that are not collinear with the bore. In one embodiment, the angle of inclination of each outlet port is between approximately 55° and approximately 65°. Stated otherwise, the angle of declination is approximately 25° to 35°. In a specific embodiment, the angle of inclination is approximately 60°, or the angle of declination is approximately 30°, as shown, for example, in FIG. 10. This embodiment provides a generally circular distribution pattern, illustrated by the arrows in FIG. 10.

One advantage of the embodiments disclosed herein utilizing a shaped nozzle with multiple outlet ports, when compared to other nozzles, is that little or no release of irrigation material is permitted without pressure being applied. For example, if a reservoir housing with a nozzle embodiment of the subject invention is tipped onto its side or even held upside-down, so that gravitational pull is directly exerted on the irrigation material, there will be little or no release of irrigation material through the outlet ports.

As mentioned above, the nozzle embodiments disclosed herein are designed to be inserted into abscess pockets or other cavities to debride and/or lavage tissues and debris therein. Thus, for the comfort of the patient and to reduce tissue damage or irritation, any and all edges that would contact tissue should be as smooth and free of sharp edges or projections as feasible. As described above, the exterior surface 106 of the nozzle itself can be tapered towards the proximal end and the gutters 101 within the exterior surface can likewise be tapered to reduce rough or sharp edges. The proximal face 250, where the outlet ports exit the nozzle, can also be configured to ease insertion of the nozzle into an abscess or other cavity.

In one embodiment, the proximal face 250 is shaped as a convex curve, such that it bows outward forming a rounded tip to the nozzle. In an alternative embodiment, the proximal face 250 is generally flat. This can ensure that the outlet ports provide sufficient pressure, volume, and dispersal pattern for efficient irrigation. However, the flat proximal face 250 can create a sharp edge with the exterior surface 106 of the nozzle. Therefore, in a further alternative embodiment, the juncture between the proximal face and the exterior surface is a beveled edge 255. In an alternative embodiment, the juncture 135 between the proximal face 250 and the exterior surface of the nozzle is a rounded edge 135. In a specific embodiment, shown, for example, in FIG. 20, the juncture is rounded to a radius of approximately 0.04 inches.

FIG. 1 shows an embodiment of the subject invention wherein the device comprises a squeezable reservoir housing 60 having a wall 61 that forms a reservoir for containing therein an irrigation material (such as abscess-irrigation material). The reservoir can preferably hold a liquid solution (for example, sterile saline solution) as the abscess-irrigation material for lavaging an abscess pocket, and thereby removing puss, dead tissue, or other contaminants from therein. The reservoir housing can have a mouth 62, which communicates the reservoir to the outside of the housing. Disposed over the reservoir housing mouth 62, and affixed to the reservoir housing mouth is a discharge apparatus 80, discussed in detail above.

Another embodiment of the subject invention includes a reservoir housing comprising an inlet port and fitting for attaching tubing for delivery of pressurized gas to the reservoir. Pressure sources generally available in hospitals, emergency rooms, and other medical clinics or facilities provide a pressure of 0-55 pounds per square inch (PSI). The reservoir can be attached by, for example, a flexible tube to the pressure source connector and to a fitting provided on the reservoir housing of the subject device.

The wall of the reservoir housing can be made from any material that is, preferably, sufficiently rigid to stand upright when the reservoir contains irrigation solution. In a typical embodiment, the reservoir housing is formed by a molded plastic, which is pliable enough to permit the wall of the reservoir housing to be squeezed or compressed by one hand to exert pressure on the contents of the reservoir. A specific embodiment comprises a plastic material that is pliable enough to squeeze by hand and which also has sufficient resilience to return to its original shape, when no longer compressed or squeezed.

The horizontal cross-sectional shape of the reservoir housing can be circular, square, rectangular, or any of a variety of other geometric shapes, as desired or available. The walls can be tapered towards one end or the other. Alternatively, other shapes can be utilized for the reservoir housing, according to, and adapted for, a particular use. For example, part of the reservoir housing wall can be slightly rounded, as in a general hourglass shape, and/or have other ergonomically shaped or molded forms or features that conform to a hand or otherwise facilitate handling or compressing the reservoir housing.

The reservoir formed by the housing of the subject invention can typically hold a volume of about 100 ml to about 1000 ml. In a particular embodiment, the reservoir can hold about 250 ml to about 750 ml. In a specific embodiment, the reservoir can hold about 500 ml. Advantageously, with manual compression, the device and method of the subject invention can deliver 500 ml of irrigation fluid in less than 30 seconds and, typically, in 15 to 25 seconds. In a further particular embodiment, the fluid is delivered at between about 4 psi and about 20 psi. Some tissues and organs, such as the eye or nose, require irrigation at lower fluid pressures. Thus, in an alternative embodiment, fluid is delivered at a pressure of between about 1 psi and about 5 psi for irrigating abscesses or wounds in more delicate tissues and organs.

To facilitate dispersal of the irrigation material, the nozzle 98 can be attached to a discharge apparatus 80 that can be affixed to the housing mouth 62, whereby the irrigation solution in the reservoir passes through the nozzle 98 to expel through the one or more outlet ports 104 in a pressurized and directional manner. Thus, in a further embodiment, the inlet port 102 of the nozzle passes through the discharge apparatus 80 such that the bore is contiguous with the mouth 62 of the reservoir housing 60.

The attachment of the discharge apparatus 80 to the reservoir neck can be permanent or removable. In one embodiment, the discharge apparatus 80 is fixedly attached to the reservoir housing mouth. In an alternative embodiment, the discharge apparatus can be detachably affixed to the reservoir housing mouth. This allows the discharge apparatus with the attached nozzle to be utilized with more than one type of reservoir housing 60 and/or irrigation material. In order to accommodate the attachment of the discharge apparatus 80, the reservoir housing can be formed with a neck portion that fully, or at least partially, circumscribes the mouth of the reservoir housing.

In one embodiment, the neck portion of the reservoir housing is generally at least slightly smaller in cross sectional area than the reservoir housing. It can also be helpful if the reservoir housing neck is integrally molded with the reservoir housing, but it can also be formed or molded separately and affixed to the mouth of the reservoir housing. The material used for the neck portion of the reservoir housing can be the same as the material used to make the reservoir housing cylinder. Alternatively, the neck portion can be a different material, such as, for example, a more rigid or sturdy material than the compressible material forming the reservoir housing wall. For example, the material used to make the neck portion can be any of a variety of materials, including, but not limited to, a metal, hard plastic, ceramic, rubber, various composites, or any other one or more suitable materials.

In a further embodiment, the neck portion and/or the discharge apparatus can include any of a variety of compatible or otherwise operably connectable features or connecting structures 82. For example, threads, latches, snap fits, grooves, pawls, interdigitating components, magnetic couplings, or other connection configurations, mechanical or otherwise, can be employed for operably connecting the reservoir housing mouth with a discharge apparatus. The connecting structures 82 can be on the outer face of the neck portion, forming a male connecting end, or they can be on the inner face forming a female connecting end of the neck portion, or some combination thereof, for attachment to the discharge apparatus.

In a specific embodiment, the discharge apparatus 80 is designed with connecting structures 82 that are threads or grooves, which allow for complementary attachment to currently available irrigation solution bottles. This embodiment allows the discharge apparatus to be interchangeable, when desired, with the screw-cap that is typically provided with irrigation solution bottles, as currently available. The screw-top design of the discharge apparatus provides the operator with the option of using the reservoir housing with the nozzle embodiments disclosed herein or to threadably remove the discharge apparatus and pour out or change the irrigation solution.

Figure 20:
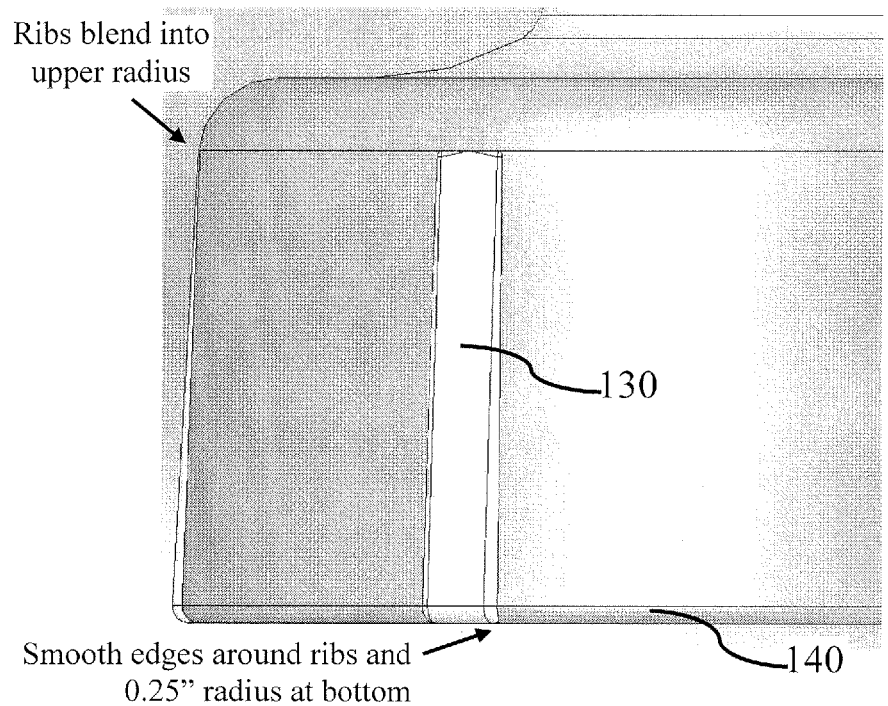
FIG. 20 is an enlarged view of the edge of the alternative embodiment of a discharge apparatus. This embodiment includes a plurality of raised ribs around the outside of the discharge apparatus to facilitate gripping or holding of the discharge apparatus, particularly if it is being transferred from one reservoir housing to another. In a further embodiment, as shown, the ribs are tapered at their proximal end, so that they blend with or are flush with the surface of the discharge apparatus. In a further embodiment, the distal end of the ribs is rounded and smooth and is contiguous with the distal end edge of the discharge apparatus.

In another embodiment, the discharge apparatus can include one or more features or structures to aid in holding or gripping the discharge apparatus. FIGS. 17, 18, and 20 illustrate an embodiment wherein one or more raised ridges or ribs 130 are formed around the periphery of the discharge apparatus. The ribs 130 can assist with gripping, turning, and holding the discharge apparatus during use or, more particularly, when the discharge apparatus is being attached to a reservoir housing 60.

In a particular embodiment, an example of which is shown in FIGS. 17, 18, and 20, the discharge apparatus is configured with a plurality of raised ribs around the outside of the discharge apparatus. In a more particular embodiment, the discharge apparatus is configured with six raised ribs, spaced equidistant apart. In a further embodiment, the ribs are tapered at the proximal end, so that they blend with or are flush with the surface of the discharge apparatus. This can provide a smooth surface near the proximal end of the discharge apparatus, which can be beneficial if there is contact with skin or tissue around the abscessed wound. In a further embodiment, the distal end of the ribs is rounded for forming a smooth transition into the distal end edge 140. In a specific embodiment, the distal end of the ribs are rounded to a radius of approximately 0.25 inches and are contiguous with the distal edge, as shown, for example, in FIG. 20.

In one embodiment, a protective backsplash shield 90 can also be included as part of either the reservoir housing or the discharge apparatus. The backsplash shield can protect the health care professional (or other user) from human and or animal body fluids mixed with the irrigation material that can be splashed from the wound during the lavaging process. In some instances, an abscess may develop deep within tissues, necessitating that the nozzle 98 be inserted deeper to reach the abscess cavity. In these situations, the backsplash shield can be nearer to, or even touching, the skin around the abscess opening.

In one embodiment, a backsplash shield 90 is a cup-like structure having a wall 93 that surrounds at least some portion of the nozzle and extends towards the proximal end 200 of the nozzle and terminates at a rim 92. FIGS. 1 through 4 illustrate one embodiment of a backsplash shield that can be used with embodiments of the subject invention. The shape of the backsplash shield can vary, but the shape should function to direct fluid and any aerosolized material away from a healthcare provider while using the irrigation device.

To prevent irrigation fluid from pooling beneath the backsplash shield, one or more run-off channels 94 can be formed within the rim 92 of the backsplash shield 90, to allow irrigation fluid to drain out.

In order that the nozzle can be inserted into an abscess, it can be advantageous for the rim 93 of the backsplash shield to terminate below the proximal end 200 of the nozzle 98. The extent to which the nozzle extends beyond the rim can vary. One factor that can determine the length of the nozzle is the depth to which it will be inserted into an abscess. Deep tissue abscesses may require that the nozzle be inserted deeper into tissue, perhaps several millimeters, than would be necessary for surface tissue abscesses, which may only require a few millimeters of depth.

In a specific embodiment, mentioned above, the nozzle extends between approximately 1.0 inch and approximately 1.3 inch beyond the rim 92 of the backsplash shield 90. In a more specific embodiment, the proximal end of the nozzle extends about 1.2 inches beyond the rim 92 of the backsplash shield, as illustrated, for example in FIGS. 1-3.

The irrigation solution used can be, for example, water, saline, or a balanced salt solution. The solution is preferably sterile and, at the discretion of the user or manufacturer of the irrigation solution, can additionally comprise an antibacterial and/or antifungal component. The device can be sterilized by known sterilization techniques, including boiling, autoclaving, gas sterilization and the like, either separately or together with the reservoir housing.

Buffered Ringer's solution or commercially available balanced salt solution (e.g., Tis-U-Sol or Physio-Sol) are physiologically compatible and are commonly used in wound irrigation procedures.

The antiseptic agents can include:

Povidone-iodine solution (Betadine preparation)—iodine added to the carrier polyvinylpyrrolidone (PVP), a water-soluble organic complex; this combination is called an iodophor. Standard solutions of Betadine preparation are 10 percent.

Povidone-iodine surgical scrub (Betadine scrub)—the iodophor PVP-I and an anionic detergent (pH 4.5).

pHisoHex—an emulsion of an anionic detergent, entsulfon, lanolin cholesterols, petrolatum, and hexachiorophene (pH 5.5).

Chlorhexidine gluconate.

Tincture of green soap-potassium oleate, isopropanol, potassium coconut oil, soap.

Dakin's solution 0.2 percent solution hypochlorite solution.

Hydrogen peroxide—an oxidizing agent.

Benzalkonium chloride (Zephiran)—a quaternary ammonium compound that works as a cationic surface active agent.

Nonionic surfactants-Pluronic F-68 (Shur-Clens) and Poloxamer-188 (Pharma Clens)—agents that have no antimicrobial activity (pH 7.1).

From the description of the device herein above, a method of using the subject device would readily be understood and adaptable by those persons having ordinary skill in the art. The reservoir housing is filled with a desired irrigation solution. The irrigation solution is sterilized before or after filling. The reservoir housing and contents can be stored in a sterile environment, e.g., sterile packaging which is opened immediately prior to use. In one embodiment, a protective shield over the nozzle is removed, then the reservoir housing can be directed towards the wound and squeezed or compressed to expel or discharge the solution in the desired direction, and at the desired pressure to effect irrigation of a wound to remove contaminants or debris.

It would also be understood that the described discharge apparatus can be packaged separately from the reservoir housing. The discharge apparatus can be further be packaged in a sterile environment. In a particular use, the discharge apparatus is provided separately from the reservoir housing, wherein the cap of a readily available, squeezable irrigation bottle containing a sterile irrigation solution, e.g., normal saline, is replaced with the subject discharge apparatus. The bottle, now having the subject discharge apparatus attached or engaged thereto, can be used as described herein In one embodiment, the discharge apparatus is provided in a sterile laceration tray. According to the subject invention, the laceration tray has, in addition to a discharge apparatus or entire irrigation bottle of the subject invention, other items conveniently provided for treating wounds. Contemplated items that can be included in a laceration tray include, but are not limited to, needle holders (i.e., 5" floor-grade smooth); scissors (i.e., 4.5" floor-grade straight Iris scissors); hemostats (i.e., 5" floor-grade curved mosquito hemostat); forceps (i.e., floor-grade tissue forceps with 1×2 teeth); cups (i.e., 2 oz. medicine cups); syringes (i.e., 10 cc Luer Lock syringe); needles (i.e., 25 gauge×⅝" needle; 27 gauge×1.5" needle; 18 gauge×1.5" needle); dressings (i.e., gauze dressings); drapes (i.e., polylined fenestrated drapes); and towels (i.e., absorbent towels).

Another embodiment of the invention provides a pressurized irrigation assembly to provide automated dispersal of irrigation solution. The pressurized irrigation assembly can comprise: irrigation solution; a reservoir housing that contains the irrigation solution; a discharge apparatus having a plurality of specifically designed nozzles through which a sufficient volume of the irrigation solution can pass at an appropriate pressure; a means for creating irrigation solution pressure for the generation of a plurality of dispersed streams through the nozzles to irrigate damaged tissue.

A variety of pressure means have been developed to enable automatic (as opposed to manual) transfer of irrigation solution from a reservoir housing. For example, U.S. Pat. No. 6,574,527 to Henniges et al. describes a hand held irrigator that can be attached to the mouth of a reservoir housing irrigation solution. Various other apparatuses that enable the automatic transfer of irrigation solution from a reservoir housing include, but are not limited to, U.S. Pat. Nos. 6,751,813; 6,746,419; 6,106,494; 5,484,402; 5,470,305; 5,269,750; and 5,046,486.

In one embodiment of the invention, the pressure means is a hand-held device similar to the irrigator disclosed in U.S. Pat. No. 6,754,527. The hand held device has a tip and a supply end. Irrigation solution from the reservoir housing is provided to the supply end of the pressure means and is eventually discharged from the tip of the pressure means Affixed to the tip is a discharge means of the invention, which can be detachably affixed to the tip. The hand held device further comprises a pump for regulating the rate of irrigation solution discharge and a motor for actuating the pump. In certain embodiments, the motor is a battery operated motor.

In a method of use, where a reservoir housing 60 having discharge apparatus 80 with a nozzle 98 affixed thereto is provided, a protective cap can first be removed from the nozzle 98 and/or backsplash shield 90. The nozzle can be directed towards the abscess incision and some portion of the proximal nozzle end inserted therein. The reservoir housing 60 can then be compressed, discharging the irrigation solution through the discharge apparatus 80. The solution can be discharged at a range of pressures of between about 4 psi and about 20 psi. In a specific embodiment, the solution is discharged with a pressure of about 7 psi.

The reservoir housing 60 can be compressed manually or via other mechanical means. For example, the operator may compress the reservoir housing using either one hand or two hands, to provide increased pressure (e.g., 16 psi). Alternatively, a pressure means, such as but not limited to, those mentioned above can be activated to generate a dispersed stream of irrigation solution through the discharge means.

In another method of use, where a reservoir housing 60 and discharge apparatus 80 with an attached nozzle 98 are provided separately, a protective cap can be removed from the mouth 62 and/or neck portion of the reservoir housing. The discharge apparatus can then be affixed to the mouth or neck portion of the reservoir housing via complementary or other connecting means. After the discharge apparatus is affixed to the reservoir housing, the nozzle thereon can be directed towards and inserted within an abscess incision. The reservoir housing can be compressed to discharge a dispersed stream of irrigation solution through one or more outlet ports within the nozzle of the discharge means.

Significantly, it is known that more force is required to rid a wound of particles with a small surface area (e.g., bacteria) than to remove particles with a large surface area (e.g., foreign debris, dead tissue, coagulated pus, etc.). Minimum recommended volumes of irrigation solution vary, but for a moderately sized abscess, for example one approximately 2 cm in diameter, at least 200 to 500 ml, or more should be used. Greater volumes, on the order of one to two liters, may be required for larger or heavily contaminated abscesses. Irrigation should continue at least until all visible, loose particulate matter has been removed.

It should be understood that the examples and embodiments described herein are for illustrative purposes only and that various modifications or changes in light thereof will be suggested to persons skilled in the art and are to be included within the spirit and purview of this application and the scope of the appended claims.

Example 1

Method of Using Abscess Debridement and Cleansing Device

As with most medical procedures, universal precautions and barrier protection should be employed when irrigating wounds, including the use of gloves, gowns, facemask, and eye protection).

A. Abscess Incise and Drainage (I&D) Procedure

1. Prepare wound site by swabbing skin overlying the abscess with an antiseptic/skin cleanser, if not contraindicated.

Figure 11:
FIG. 11 is a photograph illustrating a procedure for anesthetizing an abscessed wound.

2. Anesthetize the skin with a subcutaneous skin wheel using Lidocaine without epinephrine, if mot contraindicated. (See FIG. 11)

Figure 12:
FIG. 12 is a photograph illustrating a procedure for lacerating an abscessed wound to provide access to the abscess pocket.

3. Use a scalpel (#11 blade) to make a linear incision into the abscess cavity at the point of maximal fluctuance. (See FIG. 12)

B. Culture and Manual Removal of Abscess Exudate

4. Culture the wound, if indicated. (This is usually recommended.)

Figure 13:
FIG. 13 is a photograph illustrating a procedure for disrupting loculations that may be present within the abscessed wound.

5. Manually apply pressure to express any exudates within the abscess pocket and facilitate loculation disruption if present. (See FIG. 13)

Figure 14:
FIG. 14 is a photograph illustrating a procedure for manually expressing exudates from an abscess pocket.

6. If indicated, insert blunt instrumentation into the abscess cavity to break up loculations. (See FIG. 14)

C. Debridement and Cleansing Procedure Using Abscess Irrigation Device

7. Remove seal from irrigation fluid bottle, such as IrriSept (usually a twist or snap off seal)

8. Using clean techniques, remove sterile abscess irrigation device (LT Splatterguard™) from packaging and attach to first reservoir.

Figure 15:
FIG. 15 is a photograph illustrating use of one embodiment of the subject invention, wherein the nozzle of the discharge apparatus is inserted into the abscessed wound and fluid from the reservoir housing is expressed through the nozzle and out of the outlet ports into the abscess pocket.
Figure 16:
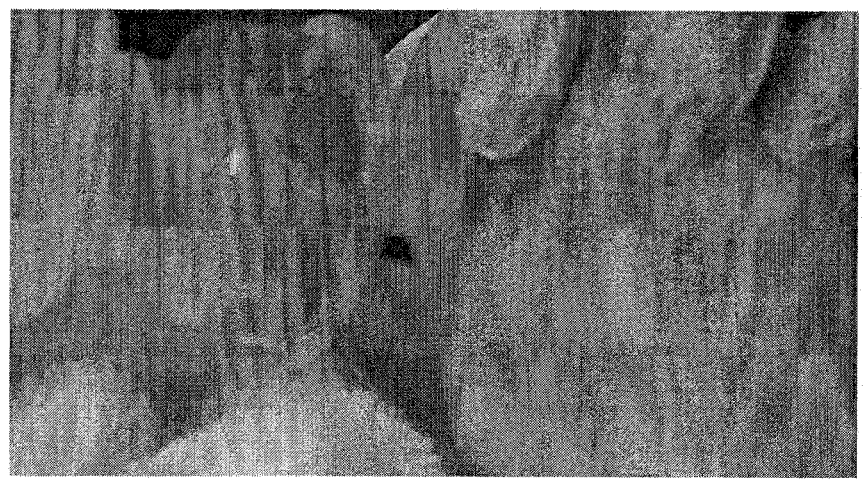
FIG. 16 is a photograph illustrating use of one embodiment of the subject invention wherein one hand is used to control the discharge apparatus and the other hand is used to manipulate the abscess pocket opening.

9. Insert the tip of the nozzle in the abscess at the incision site. (See FIG. 15)

10. Squeeze irrigation fluid from the reservoir to thoroughly cleanse the entire abscess ensuring that returning exudates is clear and the solution has contacted all inner surfaces of the abscess cavity. The nozzle tip will need to be removed to allow the bottle to recoil with air before re-inserting and continuing with cleansing.

11. Repeat until entire contents of reservoir (450 cc) has been discharged and the abscess is clear of exudates.

12. Remove nozzle tip from abscess cavity and wait approximately 1 minute before proceeding.

D. Final Cleansing and Rinse

13. Remove seal from rinsing fluid bottle, such as IrriRinse sterile saline (usually a twist or snap off seal).

14. Using clean techniques, remove sterile abscess irrigation device (LT Splatterguard™) from irrigation fluid bottle and attach to rinsing fluid bottle.

15. Insert nozzle into abscess cavity and rinse abscess using same technique described above.

E. Packing and/or Drainage

16. Pack the abscess cavity with a plain packing strip or place a drain, if indicated.

17. Apply a wound dressing directly over the abscess.

The invention claimed is:

1. An abscess irrigation device comprising:
a discharge apparatus having a proximal end, a distal end adapted to be connected to a reservoir, and an opening therebetween that communicates the distal end with the proximal end;
a rigid elongated nozzle having a distal end coupled to the proximal end of the discharge apparatus, a proximal end with a proximal face at which there are two or more outlet ports that open onto the proximal face, and a conical bore therethrough that is contiguous with the opening in the discharge apparatus and the two or more outlet ports, where the conical bore becomes narrower at the proximal end of the elongated nozzle;
at least two gutters on an exterior surface of the proximal end of the nozzle that are contiguous with the proximal face and extend towards the distal end of the nozzle to direct fluid and material out of an abscess pocket; and
a backsplash shield comprising a wall coupled to the discharge apparatus, wherein the wall extends towards the proximal end of, and at least partially surrounds, the nozzle and terminates in a rim that is between the proximal end of the discharge apparatus and the proximal end of the nozzle.

2. The abscess irrigation device, according to claim 1, wherein the proximal end of the nozzle extends between approximately 1.0 inches and approximately 1.3 inches above the rim of the backsplash shield.

3. The abscess irrigation device, according to claim 1, wherein the proximal end of the nozzle extends approximately 1.2 inches above the rim of the backsplash shield.

4. The abscess irrigation device, according to claim 1, wherein at least one of the two or more outlet ports is rectangular.

5. An abscess irrigation device comprising:
a discharge apparatus having a proximal end, a distal end adapted to be connected to a reservoir, and an opening therebetween that communicates the distal end with the proximal end;
an elongated nozzle having a distal end coupled to the proximal end of the discharge apparatus, a proximal end with a proximal face at which there are at least four outlet ports that open onto the proximal face, where at least one of the outlet ports is rectangular in cross-section, and a conical bore therethrough that is contiguous with the opening in the discharge apparatus and the at least four outlet ports, where the conical bore becomes narrower at the proximal end of the elongated nozzle;
one or more gutters on an exterior surface of the proximal end of the nozzle that are contiguous with the proximal face and extend towards the distal end of the nozzle to direct fluid and material out of an abscess pocket; and
a backsplash shield comprising a wall coupled to the discharge apparatus, wherein the wall extends towards the proximal end of, and at least partially surrounds, the nozzle and terminates in a rim that is between the proximal end of the discharge apparatus and the proximal end of the nozzle.

6. The abscess irrigation device, according to claim 5, wherein at least one outlet port has an angle of inclination that directs the outlet port away from the center of the nozzle.

7. The abscess irrigation device, according to claim 6, wherein the angle of inclination is between approximately 55° and approximately 65°.

8. The abscess irrigation device, according to claim 6, wherein the angle of inclination is 60°.

* * * * *

UNITED STATES PATENT AND TRADEMARK OFFICE
CERTIFICATE OF CORRECTION

PATENT NO. : 9,629,953 B2
APPLICATION NO. : 13/206043
DATED : April 25, 2017
INVENTOR(S) : Paul J. Rucinski It is certified that error appears in the above-identified patent and that said Letters Patent is hereby corrected as shown below:

In the Specification

<u>Column 9,</u>
Line 17, "a glitter 101" should read --a gutter 101--.

<u>Column 17,</u>
Line 30, "25 gauge×⅝" needle" should read --25 gauge × 5/8" needle--.

Lines 30-31, "27 gauge×1.5" needle" should read --27 gauge × 1.5" needle--.

Line 31, "18 gauge×1.5" needle" should read --18 gauge × 1.5" needle--.

Line 59, "means" should read --means.--.

Signed and Sealed this
Twenty-first Day of November, 2017

Joseph Matal
*Performing the Functions and Duties of the
Under Secretary of Commerce for Intellectual Property and
Director of the United States Patent and Trademark Office*